United States Patent
Peeters et al.

(10) Patent No.: US 10,119,526 B1
(45) Date of Patent: Nov. 6, 2018

(54) CONFORMAL ELECTROMECHANICAL ACTUATOR

(71) Applicant: Verily Life Sciences LLC, Mountain View, CA (US)

(72) Inventors: Eric Peeters, San Jose, CA (US); Peter Howard Smith, Pacifica, CA (US); Bejamin David Krasnow, Redwood City, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 517 days.

(21) Appl. No.: 14/964,706

(22) Filed: Dec. 10, 2015

(51) Int. Cl.
*A61B 5/02* (2006.01)
*F03G 7/06* (2006.01)
*A61B 5/00* (2006.01)
*A61B 5/022* (2006.01)
*A61M 5/20* (2006.01)

(52) U.S. Cl.
CPC .............. *F03G 7/06* (2013.01); *A61B 5/022* (2013.01); *A61B 5/683* (2013.01); *A61M 5/2053* (2013.01); *A61B 5/02* (2013.01); *A61B 5/681* (2013.01)

(58) Field of Classification Search
CPC ............ A61B 5/02; A61B 5/022; A61B 5/681
See application file for complete search history.

(56) References Cited

U.S. PATENT DOCUMENTS

2012/0046644 A1* 2/2012 Ziaie ................ A61M 5/14248
604/507
2014/0102544 A1 4/2014 Riley et al.

OTHER PUBLICATIONS

Ogden, Sam, et al. "Review on miniaturized paraffin phase change actuators, valves, and pumps." Microfluidics and nanofluidics (2013).
(Continued)

*Primary Examiner* — Puya Agahi
(74) *Attorney, Agent, or Firm* — McDonnell Boehnen Hulbert & Berghoff LLP

(57) ABSTRACT

A variety of embodiments of an at least partially flexible actuator are provided. The actuator includes a phase change material contained within an at least partially flexible enclosure of the actuator. Application of heat, using a heater of the actuator, to the phase change material causes the phase change material to boil, increasing the volume of the actuator and/or increasing a pressure within the actuator. As a result, the actuator can be used to apply a force to objects in an environment of interest. The actuator could be incorporated into a wearable blood pressure cuff and used to apply pressure to a body part of a wearer in order to detect a blood pressure of the wearer. In other examples, the actuator could be incorporated into a wearable device and used to secure a sensor or other elements of the device against skin of a wearer.

20 Claims, 6 Drawing Sheets

(56) References Cited

OTHER PUBLICATIONS

Yang, B., et al. "A latchable microvalve using phase change of paraffin wax," Sensors and Actuators, vol. 134, p. 194-200 (2007).
Ono, M., "Development of a Cylinder Type Gas-Liquid Phase-Change Actuator,".
Sim, Woo Young, et al. "A phase-change type micropump with aluminum flap valves." Journal of Micromechanics and Microengineering vol. 13, p. 286-294 (2003).
Kato, S., et al., "An Inchworm Type In-Pipe Mobile Microrobot Driven by Three Gas-Liquid Phase-Change Actuators,".
Ukai, S., et al. "Bubble driven arrayed actuator device for a tactile display." Solid-State Sensors, Actuators and Microsystems Conference, 2007. Transducers 2007. International. IEEE, 2007.

\* cited by examiner

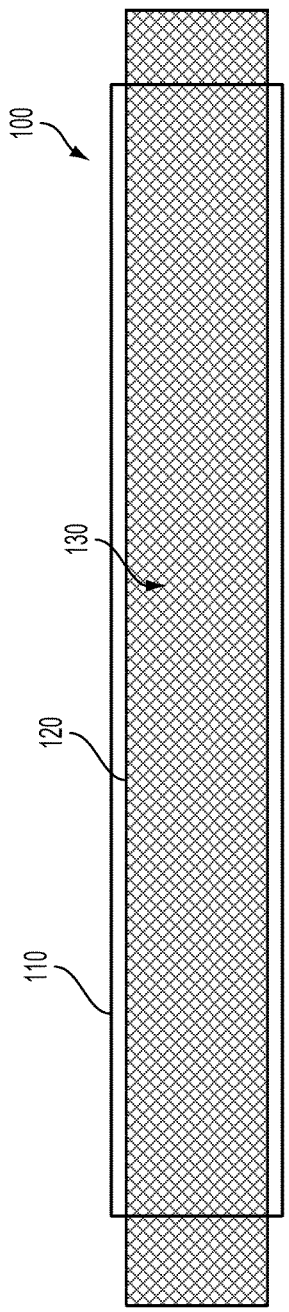
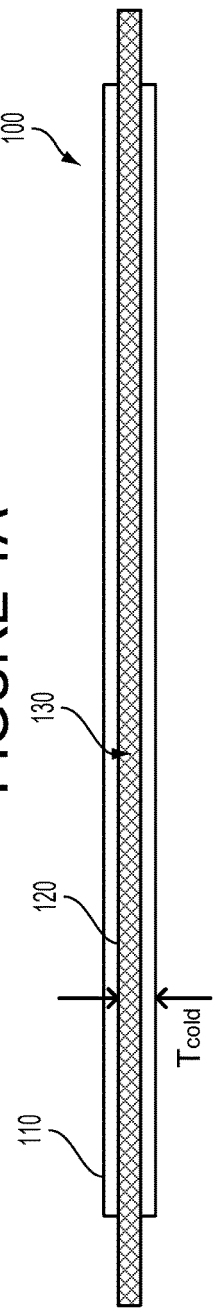
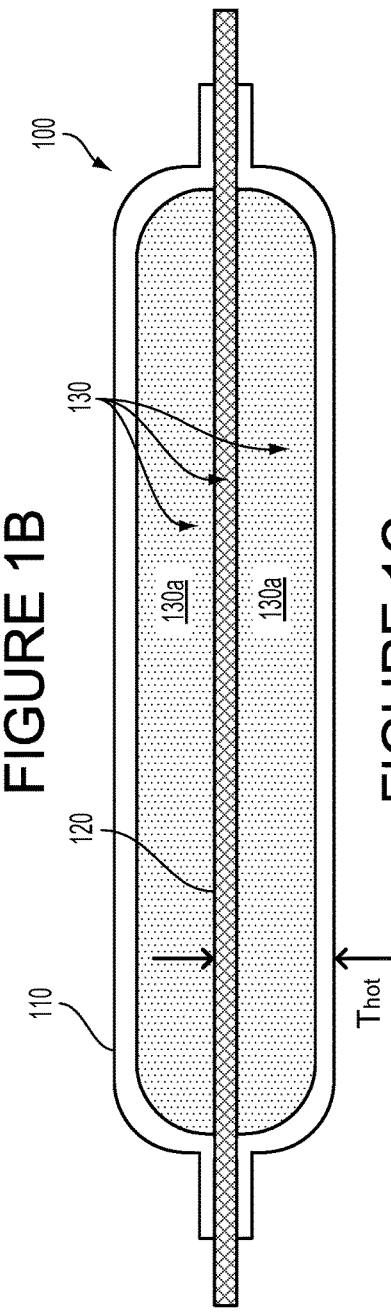
FIGURE 1A
FIGURE 1B
FIGURE 1C

미국

US 10,119,526 B1

CONFORMAL ELECTROMECHANICAL ACTUATOR

BACKGROUND

Unless otherwise indicated herein, the materials described in this section are not prior art to the claims in this application and are not admitted to be prior art by inclusion in this section.

Electromechanical actuators provide, in response to application of electrical voltages and/or currents, controllable forces, pressures, rotations, and/or displacements. Electromechanical actuators can operate by transducing an applied current and/or voltage into heat, magnetic fields, electrical fields, or some other controllable physical variables that, in turn, can be transduced into the desired mechanical actuation. Electromechanical actuators can be characterized by size, power requirements, speed, maximum angular and/or translational displacement, maximum applied force and/or torque, or other properties.

SUMMARY

Some embodiments of the present disclosure provide a body-mountable device including: (i) a mount for mounting the body-mountable device to an external body surface; (ii) a heater; (iii) a phase change material that is in contact with the heater and that changes from a liquid phase to a vapor phase in response to being heated by the heater; and (iv) an enclosure within which are disposed the heater and the phase change material, wherein the enclosure is at least partially formed from a flexible material, and wherein the phase change material changing from a liquid phase to a vapor phase in response to being heated by the heater causes at least one of (i) an increase in a volume of the enclosure such that the flexible material is displaced outward to contact the external body surface, or (ii) an increase in a pressure within the enclosure such that a force is transmitted, via the flexible material, to the external body surface.

Some embodiments of the present disclosure provide a system including: (i) a heater; (ii) a phase change material that is in contact with the heater and that changes from a liquid phase to a vapor phase in response to being heated by the heater; and (iii) an enclosure within which are disposed the heater and the phase change material, wherein the enclosure is at least partially formed from a flexible material, wherein the phase change material changing from a liquid phase to a vapor phase in response to being heated by the heater causes at least one of (i) an increase in a volume of the enclosure such that the flexible material is displaced outward, or (ii) an increase in a pressure within the enclosure such that a force is transmitted via the flexible material.

Some embodiments of the present disclosure provide a method including: (i) mounting a body-mountable device to an external body surface of a body, wherein the body-mountable device includes: (a) a mount for mounting the body-mountable device to the external body surface; (b) a heater; (c) a phase change material that is in contact with the heater; and (d) an enclosure, wherein the heater and the phase change material are disposed within the enclosure, wherein the enclosure is at least partially formed from a flexible material; and (ii) heating the phase change material using the heater such that the phase change material changes from a liquid phase to a vapor phase, wherein heating the phase change material such that the phase change material changes from a liquid phase to a vapor phase causes at least one of (i) an increase in a volume of the enclosure such that the flexible material is displaced outward to contact the external body surface, or (ii) an increase in a pressure within the enclosure such that a force is transmitted, via the flexible material, to the external body surface.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 1A is a top view of an example actuator.

FIG. 1B is a side view of the example actuator illustrated in FIG. 1A.

FIG. 1C is a side view of the example actuator illustrated in FIGS. 1A and 1B, with the example actuator having been actuated to increase a volume of the example actuator.

DETAILED DESCRIPTION

Figure 2B:
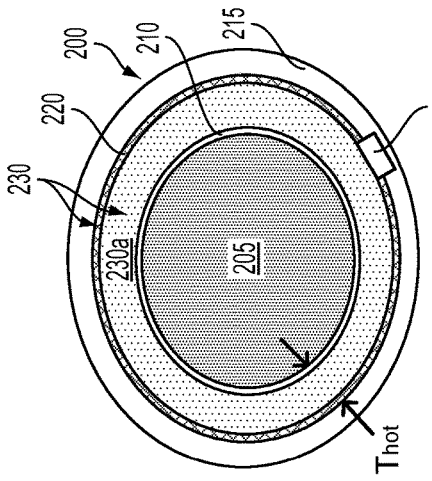
FIG. 2B is a cross-sectional view of the example device of FIG. 2A when the actuator is being operated to secure the device relative to the body part and/or to apply forces to the body part.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Further, while embodiments disclosed herein make reference to use on or in conjunction with a living human body, it is contemplated that the disclosed methods, systems and devices may be used in any environment where the operation of a device to apply a force or pressure to an environment of interest or to otherwise provide electromechanical actuation in an environment of interest is desired.

I. OVERVIEW

Electromechanical actuators may be used to provide a controllable force, displacement, torque, rotation, pressure, fluid flow, or other controlled physical variables in response to a current, voltage, or other applied electrical signals to facilitate a variety of applications. Such actuators can be characterized by a maximum generated force or torque, a maximum or range of displacement or rotation, a speed, a size, a geometry, a power requirement or efficiency, or some other characteristics. Further, in some applications, it could be beneficial for one or more elements of an actuator for be flexible, e.g., such that the actuator can be comfortably incorporated into a garment or other wearable or otherwise body-mountable devices.

In particular, portable, body-mountable applications may be facilitated by actuators that are thin, flexible, light, and that quickly provide a high amount of force and displacement while requiring minimal energy to actuate and de-actuate. For example, a wearable blood-pressure detecting cuff could be facilitated by a battery-powered actuator that provides a centimeter of displacement, applies more than 35 kilopascals of pressure onto a body part (e.g., around a wrist), and that is able to generate such displacements and pressures in less than about 10 seconds. The pressure applied by such an actuator (e.g., a pressure within a working fluid of such an actuator) could be detected as the actuator applies such a pressure, and subsequently reduces the applied pressure over time, to determine a blood pressure (e.g., a systolic blood pressure, a diastolic blood pressure) of a person. In other applications, such an actuator could be applied to appose a wearable device against a skin surface, e.g., place a sensor or other elements of the device in contact with a skin surface or to otherwise secure the location of a sensor or other device elements relative to a body part.

An actuator that is operable to provide such applications could include a heater and a phase change material disposed within an enclosure that is at least partially composed of a flexible material. The heater applying heat to the phase change material could cause the phase change material to change from a liquid to a vapor (i.e., to boil). The phase change material changing from a liquid to a vapor could, in turn, increase a pressure within the enclosure and/or increase the volume of the enclosure by displacing the flexible material(s) of the enclosure outward. Such an outward displacement of the flexible material could place the flexible material in contact with an object in the environment of the actuator, e.g., with skin of a wearer of a device that includes the actuator. Additionally or alternatively, such an increase in pressure within the enclosure could apply a force or pressure, via the flexible material, to an object in contact with the flexible material, e.g., to skin of a wearer of a device that includes the actuator.

The phase change material can be any material that is able to be boiled or otherwise changed into a vapor by application of heat by the heater and that can subsequently, when the heater is no longer providing heat and/or is providing heat at a reduced rate, change back into a liquid. For example, the phase change material could include one or more perfluoroethers, hydrofluorocarbons (e.g., perfluoropentane), and/or mixtures thereof. In some examples, the phase change material could be composed of an azeotropic mixture of multiple substances such that a boiling point of the phase change material may be controlled, e.g., by controlling the relative amounts of two or more substances in such an azeotropic mixture. A specific heat of the liquid phase, a specific heat of the vapor phase, a boiling point, a heat of vaporization, or some other properties of the phase change material could be specified according to an application. For example, the composition of the phase change material could be specified such that the specific heat of the liquid phase, the specific heat of the vapor phase, and/or the heat of vaporization are low, e.g., to reduce the amount of heat that is required to actuate the actuator by changing the phase of the phase change material and/or by increasing the pressure of a vapor phase of the phase change material. The composition of the phase change material could be specified such that the boiling point of the phase change material is a specified temperature, e.g., a temperature that is slightly higher than an operating and/or background temperature of a device including the actuator. For example, the actuator could be part of a wearable device configured to be mounted in contact with a body, and the boiling point of the phase change material could be greater than approximately 37 degrees Celsius, that is, greater than the body temperature of a wearer who may be in contact with the actuator such that the actuator is not actuated without receiving additional controllable heat via the heater.

The heater of the actuator could be configured in a variety of ways to provide a controllable amount of heat to the phase change material and/or to provide heat at a controllable rate to the phase change material. The heater could include a material that absorbs visible, infrared, electromagnetic, or other transmitted energies (e.g., an infrared absorbent material, a ferromagnetic material, a plurality of coils or loops of resistive material) and heat could be applied to the phase change material by transmitting such energies to the heater (e.g., by illuminating the heater with visible or infrared light, by exposing the heater to a radio frequency or otherwise time varying electrical, magnetic, and/or electromagnetic field). Additionally or alternatively, the heater could include resistive material (e.g., one or more wires, a conductive fabric or mesh) placed in contact with the phase change material and the phase change material could be heated by passing a current through the resistive material.

While examples and embodiments described herein refer to using a heater to change a phase change material within an enclosure in order to change the phase change material from a liquid phase to a vapor phase in order to displace outward a flexible material of the enclosure to contact skin of a body and/or to apply a force or pressure via such a flexible material to skin of a body, it should be understood that methods, devices, and other embodiments described herein could be employed to displace and/or apply forces or pressures to objects in other environments of interest.

II. EXAMPLE ACTUATORS AND OPERATION THEREOF

A heater and phase change material disposed within an at least partially flexible enclosure can be operated to provide a controllable force, pressure, and/or displacement in a variety of devices and applications. Such an actuator could provide quick, high-displacement, high force/pressure actuation in a thin, flexible form factor while requiring minimal power.

FIGS. 1A, 1B, and 1C illustrate an example actuator 100 that can be configured and/or operated as described elsewhere herein. FIGS. 1A and 1B show the actuator 100 when the actuator 100 in an un-actuated state; that is, in a state wherein the phase change material is largely in the liquid phase. FIG. 1A shows a top cross-sectional view of the actuator 100 and FIG. 1B shows a side cross-sectional view of the actuator 100. FIG. 1C shows the actuator 100 when the actuator 100 in an actuated state; that is, in a state wherein the phase change material is largely in the vapor phase.

The actuator 100 includes a heater 120 and a phase change material 130 disposed within an enclosure 110. As shown in FIGS. 1A, 1B, and 1C, the enclosure 110 is composed of a sleeve of a flexible material that is sealed to the heater 120 at either end of the actuator 100 to prevent release of the phase change material (in either the liquid or vapor phases). As the heater 120 adds heat to the phase change material 130, the phase change material 130 changes from a liquid phase to a vapor phase (illustrated in FIG. 1C by vapor phase 130a). This change can cause an increase in the volume enclosed by the enclosure 110, displacing the flexible material for the enclosure 110 outward. In an example embodiment, the heater 120 is able to absorb the liquid phase of the phase change material, minimizing the thickness of the actuator. Addition of heat, using the heater 120, to the vapor phase (e.g., 130a) of the phase change material can additionally or alternatively increase the pressure of the vapor phase within the enclosure.

Such a pressure increase could be related to the flexible material of the enclosure 110 contacting an object in the environment of the actuator 100 such that continued outward displacement of the flexible material of the enclosure 110 is resisted by the object. The increased pressure within the enclosure 110 could be transmitted as a force or pressure on such an object. Additionally or alternatively, a pressure increase within the enclosure 110 could be related to the flexible material of the enclosure 110 being displaced outward to enclose some baseline volume. Such a baseline volume could be a limitation on the total possible volume of the enclosure 110 (e.g., in examples wherein the flexible material of the enclosure 110 is substantially inelastic). Alternatively, the total volume of the enclosure could increase past the baseline volume with increasing pressure within the enclosure, e.g., in examples wherein the flexible material is elastic (e.g., composed of a rubber material).

Note that the arrangement of the elements (e.g., enclosure, heater, phase change material) of the actuator 100 is intended as a non-limiting example embodiment of an actuator as described herein. An actuator could have a different geometry (e.g., could, in the un-actuated state, comprise a thin circular, elliptical, curved, or other shape), topology (e.g., the enclosure could be branched, could be rolled up, could form a closed strip or torus), or other properties. The enclosure could be partially rigid (e.g., only one side of the enclosure could be flexible, such that a flexible material of the enclosure is displaced outward in only one direction) and/or incorporated into a housing or other elements of a device. Further, the heater and phase change material could be disposed within a more complex enclosure. For example, the enclosure could include a chamber within which are disposed the heater and some of the phase change material. The chamber could be connected, e.g., via one or more channels, to another portion of the enclosure that is at least partially formed from a flexible material that can be displaced outward and/or exert a force or pressure on objects in contact with the flexible material in response to heating of the phase change material by the heater. Such an arrangement (i.e., a chamber containing a heater and phase change material, connected to a remote region including a flexible material) could facilitate greater control of the temperature/pressure within the enclosure and/or reduce the energy cost of actuating the actuator, e.g., by isolating the heating element and/or phase change material from an environment of the actuator.

$T_{cold}$ indicates, in FIG. 1B, the combined thickness of the heater 120 and one wall of the flexible material of the enclosure 110. This thickness, and the overall thickness of the actuator 100, can be very small. Such a low overall thickness of the actuator could be related to the liquid phase of the phase change material 130 being absorbed into or otherwise contained within the heater 120, e.g., by an absorbent material of the heater 120. For example, the heater 120 could be composed of a conductive fabric or some other variety of mesh composed of a conductive material. The heater 120 and the flexible material of the enclosure 110 could be composed of very thin materials (e.g., a thin strip of conductive fabric and a thin sheet of polyester) such that the combined thickness of the heater and the flexible material, $T_{cold}$, is less than some specified thickness, e.g., less than approximately 300 microns.

The phase change material 130 could exhibit a large difference in density between the liquid phase and the vapor phase (e.g., 130a). For example, the density of the liquid phase could be approximately 1000 times the density of the vapor phase. Such a large difference could result in a large difference between the outward displacement of the actuator 100 (e.g., the thickness, $T_{hot}$, of the actuator 100 indicated in FIG. 1C) when the heater 120 is operated to change the phase change material 130 substantially fully into the vapor phase when compared to the un-actuated state of the actuator. For example, an actuator 100 having a $T_{cold}$ that is less than approximately 300 microns could, when the heater 120 is operated to heat the phase change material 130 (e.g., by applying a sufficient current through the heater 120, e.g., more than approximately 0.5 amps), expand to a thickness of approximately 1 centimeter (e.g., a $T_{hot}$ of approximately 5 millimeters). Such an expansion could occur relatively quickly, e.g., in less than approximately 10 seconds.

The phase change material 130 could include a variety of substances (e.g., perfluoroethers, hydrofluorocarbons (e.g., perfluoropentane)) that can reversibly change from a liquid phase to a vapor phase (e.g., boil or evaporate) in response to heating, and that can return from the vapor phase to the liquid phase (e.g., condense) in response to cooling (e.g., due to loss of heat to an environment and/or active cooling by a heat pump). The composition of the phase change material could be specified such that the boiling point of the phase change material is at least slightly above an expected temperature of the actuator in the non-actuated state (e.g., an ambient temperature of an environment of the actuator, an average temperature of a device that includes the actuator) such that, when the heater 120 is not applying heat to the phase change material 130, the phase change material 130 is substantially all in the liquid phase. The boiling point of the phase change material 130 could be specified as a temperature that is minimally greater than the expected temperature of the actuator in the non-actuated state, e.g., to minimize the energy necessary to actuate the actuator 100 by minimizing the temperature increase required to raise the temperature of the phase change material 130 from a non-actuated temperature to the boiling point temperature of the phase change material 130.

In examples wherein the actuator is in contact with a human body (e.g., wherein the actuator is part of a wearable and/or body-mountable device and configured to apply a pressure or force from the device onto skin of a body), the composition of the phase change material 130 could be specified such that the boiling point of the phase change material 130 is above the body temperature of the human body (e.g., greater than approximately 37 degrees Celsius) such that, when the actuator is in contact with the human body and the heater 120 is not heating the phase change material, the phase change material is substantially all in the liquid phase. For example, the phase change material 130 could include dodecafluoro-2-methylpentan-3-one (boiling point 49 Celsius). The phase change material 130 could include additives to adjust the boiling point of the phase change material 130 to a specified temperature. Additionally or alternatively, the phase change material may be composed of an azeotropic mixture of substances such that the boiling point may be specified within a range of possible boiling points.

As shown in FIGS. 1A, 1B, and 1C, the heater 120 is able to absorb the phase change material 130 when it is in the liquid phase such that the overall thickness of the actuator 100 is reduced compared to a configuration wherein the liquid phase is not able to be absorbed or otherwise stored within the heater 120. In such alternative configurations, the phase change medium, in the liquid phase, could be stored in a volume within the enclosure 110 that is between the heater 120 and the enclosure 110, within a reservoir (not shown) that is connected to the enclosure, or disposed in some other location or structure such that the heater 120 can apply heat to the liquid phase of the phase change material 130 to change the phase change material 130 into the vapor phase. Additionally or alternatively, holes, slots, or other features could be formed in the heater 120 to provide reservoirs for the storage of the liquid phase of the phase change material 130.

The heater 120 could be composed of one or more resistive wires or other elements configured to provide heat when current and/or voltage is applied to the resistive wires. In a preferred embodiment, the heater 120 includes a conductive fabric or some other configuration of a mesh of material having an appropriate electrical conductivity. A conductive fabric or other conductive mesh can increase the surface area over which the liquid phase of the phase change material 130 contacts the heater 120, increasing the rate at which the heater 120 can add heat to the phase change material 130 (e.g., to increase the rate at which the phase change material 130 changes from the liquid phase to the vapor phase in response to the applied heat). Further, such an increase in the surface area of the heater 120 could reduce the occurrence of 'hot spots' at which the temperature of the phase change medium 130, heater 120, and/or enclosure 110 are significantly higher than other regions at which the heater 120 is providing heat, reducing the likelihood of the heater 120, phase change material 130, or enclosure 110 undergoing an irreversible thermal process (e.g., melting, burning, thermally decomposing, an endothermic and/or exothermic chemical reaction, denaturation, warping). A heater 120 composed of a fabric or other conductive mesh could also provide a high degree of flexibility. The heater 120 could be composed of a mesh or fabric of solid and/or stranded wires, of metal-coated fibers (e.g., nylon or polyester fibers, coated with a metal coating (e.g., by sputtering) and woven into a fabric or other mesh), or strands of some other flexible conductive material.

Note that a heater of an actuator as described herein could be configured to provide heat by some other means. For example, the heater could include energy-absorbing materials or structures that operate to transduce a received energy (e.g., visible light, infrared light, time-varying electrical, magnetic, and/or electromagnetic fields) into heat that can be provided to a phase change material in contact with the heater. For example, the heater could include an optically absorbing material and energy could be transmitted to the heater in the form of visible light, infrared light, or some other wavelengths of light. In another example, the heater could include a conductive material, a magnetic material, a number of loops or coils of conductive material, or some other materials or structures that can be heated by transmission of a time-vary electrical, magnetic, and/or electromagnetic field (e.g., a radio frequency electromagnetic field or some other time-varying electric and/or magnetic field) to the heater.

As shown in FIGS. 1A, 1B, and 1C, the enclosure 110 could be composed entirely of flexible materials. Alternatively, an enclosure of an actuator as described herein could be only partially composed of flexible materials. For example, the heater 120 and phase change material 130 of the actuator 100 could be disposed on a flat, curved, or otherwise shaped rigid element and a flexible material could then be secured to the rigid element over the heater 120 and phase change material 130. Such flexible materials could be substantially inelastic (e.g., a polyester film). Alternatively, such flexible materials could be elastic (e.g., a rubber). Use of an elastic flexible material could provide an actuator having a smoother actuation over a greater range of displacements/stroke lengths/volumes at a lower force/pressure than an actuator that includes an inelastic flexible material.

The flexible material could be composed of a material that is substantially impermeable to the phase change material 130 in the liquid phase and the vapor phase, in order to prevent the phase change material 130 from escaping the enclosure 110 over time. Additionally or alternatively, the flexible material could include a lining composed of one or more materials that are substantially impermeable to the phase change material 130 in the liquid phase and the vapor phase, e.g., a lining composed of a metal and/or a metal oxide. Such a lining could be formed as a foil that is adhered or otherwise disposed as part of the flexible material (e.g., an aluminum foil disposed on a polyester film) and/or such a lining could be sputtered, vapor-deposited, or otherwise formed on a sheet of flexible material (e.g., a barrier film composed of thin layer of metal or inorganic metal oxide that is sputtered, chemical vapor deposited, or otherwise formed on a polyester film or some other flexible material).

An actuator as described herein could include additional or alternative elements to those shown in FIGS. 1A, 1B, and 1C. For example, an actuator could include layers of insulating material to control the flow of heat into and out of the actuator. This could include the flexible material or other elements of an enclosure of the actuator being composed of thermally insulating material and/or could include such materials being disposed outside of the actuator (e.g., disposed as a layer of insulating material located on a flexible material of the enclosure). Such insulating materials could include aerogels, fabrics (e.g., wool, felt), polymer foam, or some other flexible or rigid insulating materials. Such insulating materials could be provided to increase the efficiency, speed, and/or force of operation of the actuator by, e.g., reducing heat flux from the phase change material into the environment of the actuator. Insulating materials could be provided to protect a user's skin or some other object from the increased temperature of the vapor phase of the phase change material. Insulating materials could be provided to prevent actuation of the actuator without operation of the heater, e.g., by preventing heat from the environment of the actuator (e.g., from skin of a person's body) from increasing the temperature of the phase change material.

The temperature of the phase change material 130 could be controlled through additional means. In some examples, the actuator 100 could include a heat pump configured to controllably remove and/or add heat energy from/to the phase change material 130. Such a heat pump could include a Peltier device, a thermoelectric cooler, or some other elements configured to controllably remove heat from the phase change material 130. Such a heat pump could be operated in combination with the heater 120 to control the outward displacement of the flexible material of the enclosure 110, to control a pressure within the enclosure 110, and/or to control a pressure or force applied on objects in an environment (e.g., on skin of a person) via the flexible material. For example, the heater 120 could be used, during a first period of time, to add heat to the phase change material to outwardly displace the flexible material of the enclosure 110 and/or to increase a force or pressure exerted via the flexible material. The heat pump could be used, during a second period of time, to remove heat from the phase change material to inwardly displace the flexible material of the enclosure 110 and/or to decrease a force or pressure exerted via the flexible material.

In some examples, an actuator as described herein (e.g., 100) could include a pressure sensor that is configured to detect a pressure of the phase change material within an enclosure of the actuator. Such a sensor could be disposed within the enclosure, connected to a port or channel of the enclosure, or otherwise connected to the enclosure such that the pressure within the enclosure can be detected. A pressure within the enclosure, detected using the pressure sensor, could be used to control the pressure within the enclosure and/or to control a pressure or force exerted on elements in the environment by a flexible material of the enclosure. This could include using feedback control, based on the detected pressure, to control the amount and/or rate of heat delivery to the phase change material of the actuator in order to, e.g., maintain the pressure within the enclosure at a specified pressure, within a specified range of pressures, or according to some other consideration. Additionally or alternatively, the detected pressure could be used to detect a property of the environment of the actuator, e.g., to detect a force or pressure exerted on the actuator via the flexible material. For example, the actuator could be used to apply a range of pressures to a body part (e.g., to a wrist) over time, and the pressure within the enclosure over time could be used to determine a blood pressure.

An actuator as described herein (e.g., actuator 100) could be configured a variety of ways and integrated into a variety of devices or systems according to an application. In some examples, the actuator could be integrated into a wearable or otherwise body-mountable device and operable to apply a force or pressure on the body, e.g., to detect a property of the body (e.g., to detect a compliance of skin, to detect a blood pressure), to control the location of a body part relative to the device (e.g., to control the location of skin relative to a sensor, injector, or other device elements), to provide haptic feedback, to provide assistive forces, to reduce blood flow (e.g., to reduce blood loss due to an injury), or to provide some other applications. Actuators as described herein could be configured to provide additional functions, e.g., to extend an antenna or other elements of a device, to change a size or geometry of a device, to change a buoyancy of a device, or to provide some other functionality.

A wearable or otherwise body-mountable device that includes an actuator as described herein could be configured to fully or partially enclose a body part (e.g., to fully or partially enclose a wrist, an arm, an ankle, a leg). The actuator of such a device could itself be configured to fully or partially enclose the body part. For example, an actuator and/or body-mountable device could be configured to substantially fully enclose a body part in order, e.g., to apply a range of pressures to detect a blood pressure, in order to prevent or reduce blood flow into and/or out of the body part, to center the body part within the body-mountable device, or to provide some other functionality. In other examples, the actuator could provide force to only a portion of the body part, e.g., to apply force on one side of the body part. Such an applied force could be provided such that the opposite side of the body part is pressed against a sensor, an injector, or some other aspect of the body-mountable device and/or such that the location of the body part relative to a sensor, an injector, or some other aspect of the body-mountable device is secured.

Figure 2A:
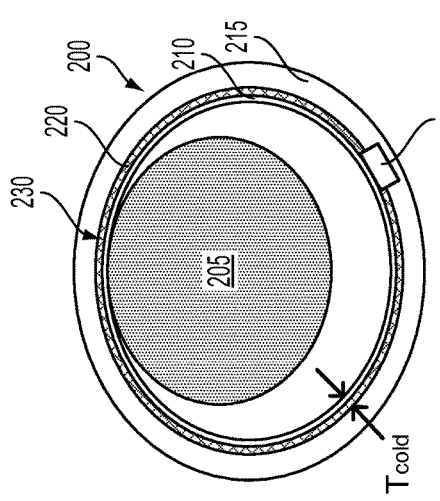
FIG. 2A is a cross-sectional view of an example device mounted around a body part.

FIGS. 2A and 2B illustrate an example wearable device 200 that fully encloses a body part 205 (e.g., a wrist, a limb). The device 200 includes a housing 215 that forms, in combination with a flexible material 210, an enclosure of an actuator of the device 200. The housing 215 may be composed of a flexible material, such that the device 200 is, overall, rigid, or the housing 215 may be composed of a flexible material such that the device 200 is, in general, flexible and thus may conform to the shape of the body part 205. The actuator additionally includes a heater 220. The heater 220 contains a phase change material 230. This could include the heater 220 being formed with phase change material-containing reservoirs or the heater 220 being composed of an absorbent material (e.g., a conductive fabric) into which the phase change material 230 is absorbed. The device 200 additionally includes a pressure sensor 250 that can be used to detect a pressure of the phase change material 230 within the enclosure of the actuator.

FIG. 2A shows the device 200 when the actuator in an un-actuated state; that is, in a state wherein the phase change material 230 is largely in the liquid phase and absorbed into the heater 230. In this state, the actuator is thin (the combined thickness of the heater 230 and flexible material 210 indicated by $T_{cold}$) as disposed against the inner surface of the housing 215. FIG. 2B shows the device when the actuator in an actuated state; that is, in a state wherein the phase change material 230 is largely in the vapor phase 230a due at least in part to heating of the phase change material 230 by the heater 220. The actuator has increased in thickness (indicated by $T_{hot}$); that is, the flexible material 210 has been displaced outward from the device 200 to contact skin of the body part 205. The flexibility of the flexible material 210 allows the flexible material 210 to conform to the outer surface of the body part 205.

The heater 220 could be operated to apply a specified pressure or force on the body part 205 by controlling a pressure of the phase change material 230 that, in turn, applied a force or pressure on the body part 250 via the flexible material 210. Such a pressure could be applied to reduce or stop a flow of blood in the body part, e.g., to prevent blood loss from a wound distal to the location of the device 200, to reduce blood flow to allow for calibration of a blood flow based (e.g., an ultrasonic blood flow sensor of the device 200) blood pressure sensor (e.g., by controlling and/or detecting the pressure in the body part 205 using the pressure sensor 250) or to provide some other functionality. In some examples, the heater 220 could be operated to provide heat to the phase change material 230 at a time-varying rate such that the flexible material 210 is displaced outward to contact an external body surface (e.g., skin) of the body part 205 and to apply a range of pressures to the body part 205. The range of applied pressures includes pressures greater than an expected maximum blood pressure (e.g., greater than approximately 35 kilopascals). The pressure within the enclosure (e.g., the pressure of the vapor phase 230a of the phase change material 230) could be detected over time as the pressure applied by the flexible material 210 changes and a blood pressure could be determined based on the detected pressure over time.

In a particular example, the heater 220 could be operated, during a first period of time, to apply heat to the phase change material 230 at a first rate such that the flexible material 210 is displaced outward to contact an external body surface of the body part 205 and further such that a force is transmitted, via the flexible material 210, to the external body surface. The heater 220 could then be operated, during a second period of time, to apply heat at a second rate to the phase change material 230. The second rate is less than the first rate, and is sufficiently less than the first rate such that force transmitted, via the flexible material 210, to the external body surface decreases over time during the second period of time. This could include providing substantially no heat during the second period of time (that is, the second rate could be substantially zero). The pressure sensor 250 could be operated, during at least one of the first and second periods of time, to measure the pressure within the enclosure of the actuator (e.g., the pressure of the vapor phase 230a of the phase change material 230) and these pressure measurements could be used to determine a systolic blood pressure, a diastolic blood pressure, or some other metric of the blood pressure of a person.

This determination could include determining, based on the detected pressure measurements, a systolic blood pressure based on a determined average pressure above which oscillatory patterns in the detected pressure cannot be detected (e.g., due to complete constriction of blood flow in the body part 205 by forces exerted on the body part 205 by the device 200). Additionally or alternatively, determination of a blood pressure could include determining, based on the detected pressure measurements, a diastolic blood pressure based on a determined average pressure below which oscillatory patterns in the detected pressure cannot be detected (e.g., due to the pressure exerted by the device 200 being too low for changes in pressure related to the blood flow in the body part 205 to be transduced into changes in the pressure within the enclosure of the actuator). Determining a blood pressure of a person, using actuators or other systems or apparatus described herein, could include applying a variety of oscillometric techniques.

The device 200 and actuator (i.e., the heater 220 and phase change medium 230 disposed within an enclosure at least partially formed from the housing 215 and the flexible material 210) shown in FIGS. 2A and 2B are both configured to fully enclose the body part 205. However, actuators and body-mountable devices including such actuators as described herein could be configured to only partially enclose a body part. For example, a device could be C-shaped and able to be mounted around a body part (e.g., a wrist). Additionally or alternatively, an actuator of a device could be configured to only partially enclose a body part, e.g., to allow a housing or other elements to which the actuator is attached to include a clasp or other closure. In some examples, a device could include an actuator configured to apply forces to only a small part of a body part and/or a small area of an external body surface. Such an actuator could be configured, e.g., to press a body part against another part of a device (e.g., a sensor on an opposite side of the device) or to otherwise apply a force to secure the location of a body part relative to elements of a device.

Figure 3:
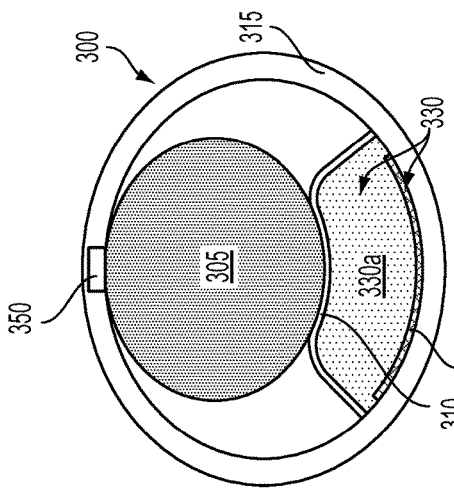
FIG. 3 is a cross-sectional view of an example device mounted around a body part.

As an illustrative example, FIG. 3 shows a wearable device 300 that fully encloses a body part 305 (e.g., a wrist, a limb). The device 300 includes a housing 315 that forms, in combination with a flexible material 310, an enclosure of an actuator of the device 300. The actuator additionally includes a heater 320. The heater 320 may contain a phase change material 330 when such a phase change material is in a liquid phase. The device 300 additionally includes a payload 350. The payload 350 could include a sensor, an injector, a blood sampling element, a lancet, and/or some other elements that can be operated to provide some functionality when in contact with skin of a body part (e.g., 305) and/or when the location of the payload 350 relative to the body part 305 (e.g., relative to a portion of subsurface vasculature of the body part 305, relative to an external body surface of the body part 305, relative to a tendon, nerve, implant, or other target within the body part 305).

FIG. 3 shows the device 300 when the actuator in an actuated state; that is, in a state wherein the phase change material 330 is largely in the vapor phase 330a due at least in part to heating of the phase change material 330 by the heater 320. As shown in FIG. 3, the actuator does not fully enclose the body part 305; instead the flexible material 310 of the actuator contacts an external body surface of the body part 305 on only one side of the body part 305. That is, the flexible material 310 has been displaced outward from the device 300 to contact skin on one side of the body part 305. The actuator is exerting, via the flexible material 310, a force on the external body surface of the body part 305 such that the location of the payload 350 is secured relative to the body part 305 (e.g., relative to an area of skin opposite the location at which the flexible material 310 is contacting the body part 305). In such a configuration, the payload 350 could be operated to provide some functionality.

In some examples, the payload 350 could include a sensor. The operation of the sensor could be conditional on element(s) of the payload 350 being in contact with skin of the body part 305 (e.g., an ultrasonic transducer of an ultrasonic flow transducer, electrodes of an electrocardiographic, galvanic, or other electrophysiological sensor). Additionally or alternatively, the operation of the sensor could be improved (e.g., a resolution, a noise level, an accuracy) when the location of the sensor relative to the body part 305 and/or elements thereof (e.g., a portion of subsurface vasculature, a tendon, a nerve, an area of skin, an implant) is controlled using an actuator as described elsewhere herein.

In some examples, the payload 350 could include an injector that is configured to penetrate skin of the body part 305 with a needle. In some examples, the needle could penetrate the skin to deliver a drug. Such a drug could be disposed on the outside of the needle, or could be delivered from a reservoir via a channel within the needle. Additionally or alternatively, the needle could be used to deliver a small device (e.g., an active electronic device, a drug eluting device, a probe that include an optically or otherwise detectable contrast agent or reagent). In some examples, the needle could penetrate the skin in order to extract a sample of blood from the skin. Such a sample could be presented to a sensor of the device 300 to detect some property of the blood and/or the blood could be directed to a storage reservoir of the device 300 (e.g., via capillary effects to a storage capillary tube coated with an anti-clotting agent, e.g., heparin). In some examples, the device 300 could be configured to apply suction (e.g., from an evacuated volume of the device 300 that is, e.g., penetrated by the needle being driven by the injector through a vacuum seal and on into the skin) to draw blood out of the skin after the skin has been penetrated by the needle. An injector could be configured to provide a variety of different functionalities.

III. EXAMPLE DEVICES

An actuator as described herein can be included as part of device configured to be mounted to an external body surface of a wearer. Such a device could be configured to enable a variety of applications and functions including, by operating the actuator to apply forces and/or pressures to an external body surface of a wearer, detecting a blood pressure, fully or partially reducing blood flow in the body part, securing the location of a sensor (e.g., to detect a property of the wearer's body), injector (e.g., to inject a device or substance into the wearer's body, to access a blood sample from the wearer's body), or other elements of the device relative to the body part, or performing some other functions. Such devices could enable a variety of applications, including measuring physiological information about a person, indicating such measured information or other information to the person (e.g., using a vibrator, a screen, a beeper), recording such information, indicating such information to a remote system (e.g., a server in a physician's office), or other functions.

Figure 4:
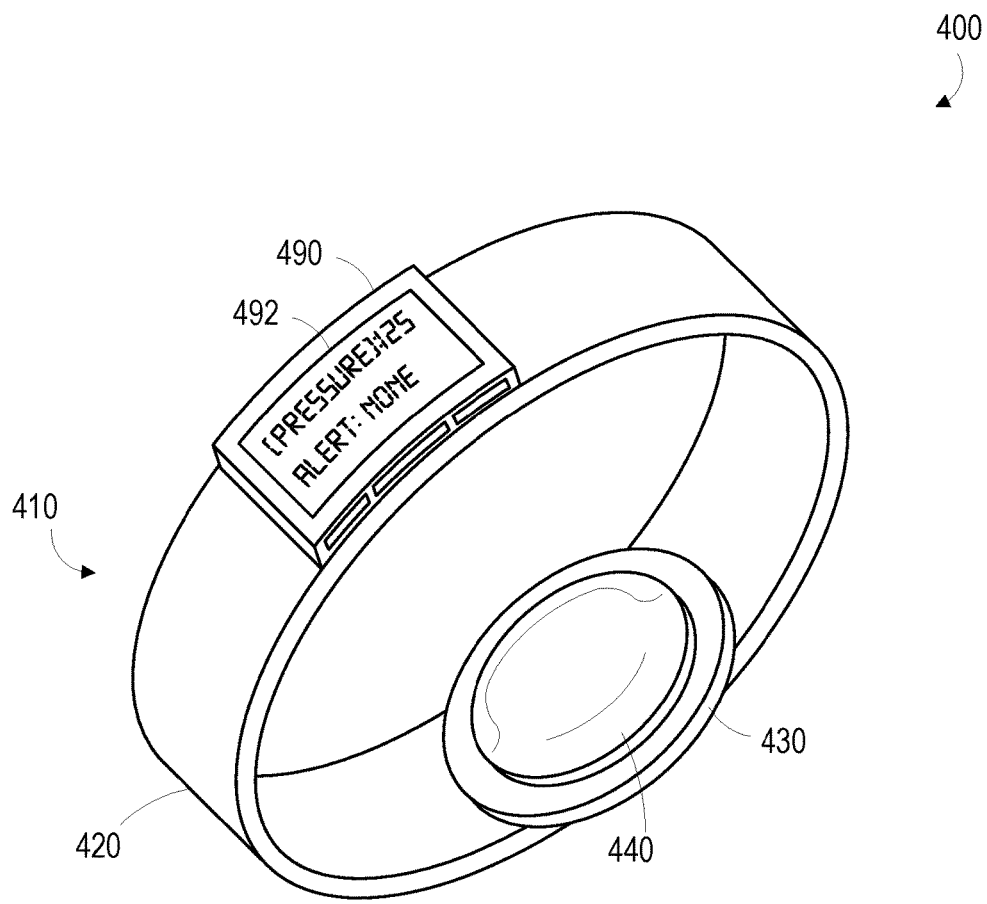
FIG. 4 is a perspective view of an example body-mountable device.

An example of a wearable body-mountable device 400 that includes an actuator as described elsewhere herein is illustrated in FIG. 4. The term "wearable device," as used in this disclosure, refers to any device that is capable of being worn at, on or in proximity to a body surface, such as a wrist, ankle, waist, chest, or other body part. In order to take in vivo measurements in a non-invasive manner from outside of the body, to inject devices or substances in a target tissue, access blood samples from a portion of subsurface vasculature, or to facilitate some other applications the wearable device may be positioned on a portion of the body where a target tissue or structure is located (e.g., a portion of subsurface vasculature, a particular artery or vein), the qualification of which will depend on the application and type of sensor, injector, or other element(s) used. The device may be placed in close proximity to skin or tissue, but need not be touching or in intimate contact therewith. A mount 410, such as a belt, wristband, ankle band, etc. can be provided to mount the device at, on or in proximity to the body surface. The mount 410 may prevent the wearable device from moving relative to the body to reduce measurement error and noise. Alternatively, the mount 410 may allow the device 400 to be mounted loosely around a body part (e.g., a wrist), providing for increased comfort and/or permitting relative motion between the device 400 and skin or other elements of a body part. In one example, shown in FIG. 4, the mount 410, may take the form of a strap or band 420 that can be worn around a part of the body.

An actuation platform 430 is disposed on the mount 410 such that it can be positioned on the body where a force may be exerted on an external body surface to facilitate some functionality of the device 400. A flexible material 440 forms part of an enclosure of an actuator of the actuation platform 430. Within the enclosure of the actuator are disposed a heater and a phase change material. For example, the heater could be disposed immediately beneath the flexible material 440. The actuator can be operated, by using the heater to apply heat to the phase change material such that the phase change material changes from a liquid phase to a vapor phase, to displace the flexible material 440 outward (as shown in FIG. 4) to, e.g., contact a skin surface of a wearer and further to apply a force and/or pressure to such a contacted skin surface. The actuation platform 430 may include a pressure sensor configured to detect a pressure within the actuator. Such a detected pressure can be used to control the exerted force, exerted pressure, and/or displacement of the actuator. Additionally or alternatively, such a detected force can be used to determine a blood pressure (e.g., by detecting the pressure as the pressure exerted by the actuator against a body part changes across a range of values), to calibrate a flow-based blood pressure sensor (e.g., by correlating a change in a detected blood flow rate with changes in the applied pressure on a body part), or to facilitate some other functionality.

The device 400 may include sensors, injectors, or other elements that can be operated in combination with the actuator. Operation of the actuator to apply a force to a body part could secure the location of such elements of the device relative to the body part (e.g., to reduce motion artifact or otherwise improve operation of a sensor to detect a physiological property), could maintain such elements in contact with the body part, or could provide some other functionality. For example, the actuator could be operated to maintain electrodes of an electrocardiographic, galvanic, or other electrophysiological sensor in contact with skin of a body part. In another example, the actuator could be operated to maintain an ultrasonic transducer of a sensor (e.g., an ultrasonic blood flow sensor) in contact with skin of the body part. In yet another example, the actuator could be operated to maintain an injector in contact with skin of the body part. The injector could be configure to drive a needle to penetrate skin of the body part, when the actuator is exerting force to maintain the injector in contact with the skin of the body part. Such an injector could be configured to deposit a device or substance in the skin (e.g., a drug, a micro-electronic sensor and/or stimulator, an optical or otherwise configured transducer that can be interrogated from outside the skin, e.g., by a sensor of the device 400). Additionally or alternatively, such an injector could be configured to access a blood sample from the skin (e.g., to detect a property of the accessed blood using a sensor of the device 400 and/or to store the accessed blood in the device 400 for later use).

The wearable device 400 may also include a user interface 490 via which the wearer of the device may receive one or more recommendations or alerts generated either from a remote server or other remote computing device, or from a processor within the device. The alerts could be any indication that can be noticed by the person wearing the wearable device. For example, the alert could include a visual component (e.g., textual or graphical information on a display), an auditory component (e.g., an alarm sound), and/or tactile component (e.g., a vibration). Further, the user interface 490 may include a display 492 where a visual indication of the alert or recommendation may be displayed. The display 492 may further be configured to provide an indication of any measured physiological parameters, for instance, a determined blood pressure.

Figure 5:
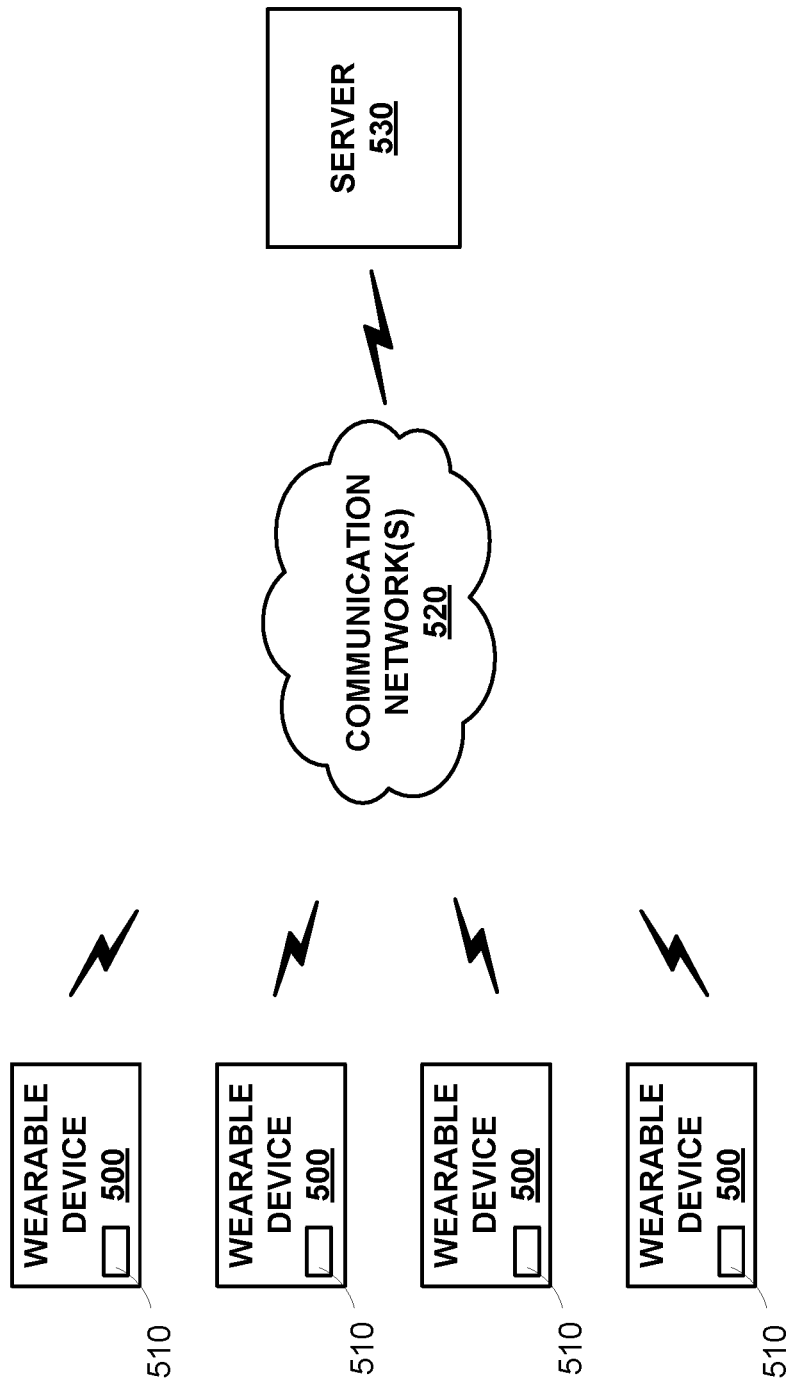
FIG. 5 is a block diagram of an example system that includes a plurality of wearable devices in communication with a server.

FIG. 5 is a simplified schematic of a system including one or more wearable devices 500. The one or more wearable devices 500 may be configured to transmit data via a communication interface 510 over one or more communication networks 520 to a remote server 530. In one embodiment, the communication interface 510 includes a wireless transceiver for sending and receiving communications to and from the server 530. In further embodiments, the communication interface 510 may include any means for the transfer of data, including both wired and wireless communications. For example, the communication interface may include a universal serial bus (USB) interface or a secure digital (SD) card interface. Communication networks 520 may be any one of may be one of: a plain old telephone service (POTS) network, a cellular network, a fiber network and a data network. The server 530 may include any type of remote computing device or remote cloud computing network. Further, communication network 520 may include one or more intermediaries, including, for example wherein the wearable device 500 transmits data to a mobile phone or other personal computing device, which in turn transmits the data to the server 530.

In addition to receiving communications from the wearable device 500, such as collected physiological parameter data and data regarding health state as input by the user, the server may also be configured to gather and/or receive either from the wearable device 500 or from some other source, information regarding a wearer's overall medical history, environmental factors and geographical data. For example, a user account may be established on the server for every wearer that contains the wearer's medical history. Moreover, in some examples, the server 530 may be configured to regularly receive information from sources of environmental data, such as viral illness or food poisoning outbreak data from the Centers for Disease Control (CDC) and weather, pollution and allergen data from the National Weather Service. Further, the server may be configured to receive data regarding a wearer's health state from a hospital or physician. Such information may be used in the server's decision-making process, such as recognizing correlations and in generating clinical protocols.

Additionally, the server may be configured to gather and/or receive the date, time of day and geographical location of each wearer of the device during each measurement period. Such information may be used to detect and monitor spatial and temporal spreading of diseases. As such, the wearable device may be configured to determine and/or provide an indication of its own location. For example, a wearable device may include a GPS system so that it can include GPS location information (e.g., GPS coordinates) in a communication to the server. As another example, a wearable device may use a technique that involves triangulation (e.g., between base stations in a cellular network) to determine its location. Other location-determination techniques are also possible.

The server may also be configured to make determinations regarding a blood pressure or other detected physiological parameters of a user based on information received from one or more of the wearable devices 500 that are associated with the user. This could include receiving signals detected by multiple sensors (e.g., pressure sensors) of a single wearable device 500 and/or receiving signals from multiple devices 500 and using the received signals to determine the pulse rates. The server may also be configured to make determinations regarding drugs or other treatments received by a wearer of one or more of the devices 500 and, at least in part, the physiological parameter data and the indicated health state of the user. From this information, the server may be configured to derive an indication of the effectiveness of the drug or treatment. For example, if a wearer is prescribed a drug intended to treat hypertension, but the server receives data from the wearable device(s) indicating (based on detected blood pressure values) that the wearer's blood pressure has remained elevated over a certain number of measurement periods, the server may be configured to derive an indication that the drug is not effective for its intended purpose for this wearer.

Further, some embodiments of the system may include privacy controls which may be automatically implemented or controlled by the wearer of the device. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

IV. EXAMPLE ELECTRONICS

Figure 6:
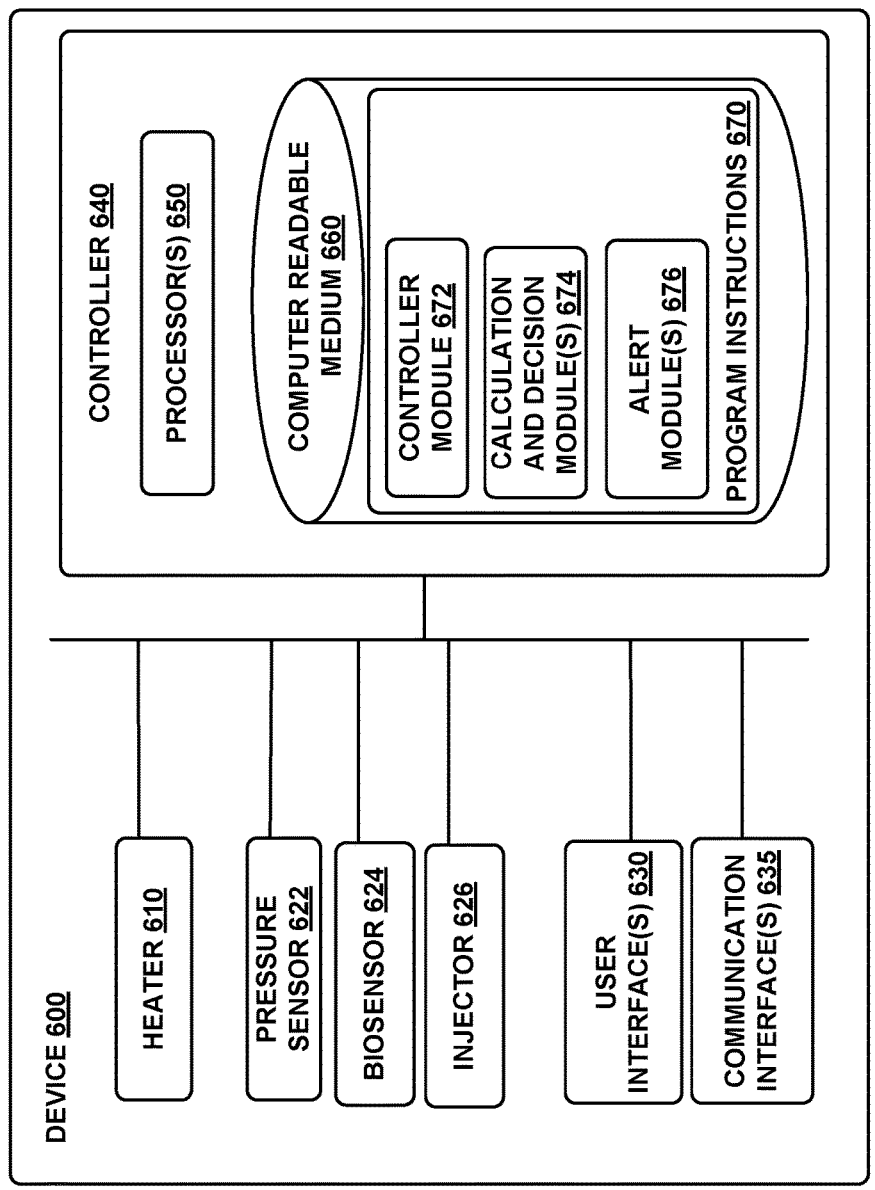
FIG. 6 is a functional block diagram of an example device.

FIG. 6 is a simplified block diagram illustrating the components of a device 600, according to an example embodiment. Device 600 may take the form of or be similar to one of the actuator-including, body-mountable devices 200, 300, or 400 shown in FIGS. 2A, 2B, 3, and 4. However, device 600 may also take other forms, such as an ankle, waist, or chest-mounted device. Device 600 could also take the form of a device that is not configured to be mounted to a body. For example, device 600 could take the form of a device configured to be maintained in proximity to a body part by a user or operator of the device 1000 or by a frame or other supporting structure. Device 600 also could take other forms.

In particular, FIG. 6 shows an example of a device 600 having an actuator including a heating element 610 and a phase change material disposed within an enclosure that is composed, at least partially, of a flexible material as described elsewhere herein. A pressure sensor 622 is configured to detect a pressure within the enclosure of the actuator (e.g., a pressure of a vapor phase of the phase change material). The device 600 additionally includes a biosensor 624 and an injector 626 having locations that can be secured, relative to a body part of a user, by application of force and/or pressure on the body part by the actuator. The device 600 additionally includes a user interface 630, communication interface 635 for transmitting data to a remote system, and a controller 640. The components of the device 600 may be disposed on a mount or on some other structure for mounting the device to enable operation related to a body part and/or tissues of interest, for example, mounting to an external body surface where one or more portions of subsurface vasculature or other anatomical elements are readily accessible.

Controller 640 may be provided as a computing device that includes one or more processors 650. The one or more processors 650 can be configured to execute computer-readable program instructions 670 that are stored in the computer readable data storage 660 and that are executable to provide the functionality of a device 600 described herein.

The computer readable medium 660 may include or take the form of one or more non-transitory, computer-readable storage media that can be read or accessed by at least one processor 650. The one or more computer-readable storage media can include volatile and/or non-volatile storage components, such as optical, magnetic, organic or other memory or disc storage, which can be integrated in whole or in part with at least one of the one or more processors 650. In some embodiments, the computer readable medium 660 can be implemented using a single physical device (e.g., one optical, magnetic, organic or other memory or disc storage unit), while in other embodiments, the computer readable medium 660 can be implemented using two or more physical devices.

The program instructions 670 stored on the computer readable medium 660 may include instructions to perform any of the methods described herein. For instance, in the illustrated embodiment, program instructions 670 include a controller module 672, calculation and decision module 674 and an alert module 676.

The controller module 672 may include instructions for operating the heating element 610 to heat the phase change material of the actuator and thus to displace a flexible material of the actuator outward (e.g., to contact an external body surface of a user) and/or to exert a force or pressure, via the flexible material, on an object in the environment of the device (e.g., on an external body surface in contact with the flexible material). The controller module 672 may additionally include instructions for operating the pressure sensor 622, the biosensor 624, and/or the injector 626. For example, the controller module 672 may include instructions for operating the pressure sensor 622 to detect the pressure within the actuator at a plurality of points in time, e.g., to provide information to determine a blood pressure, to control (e.g., via negative feedback) a pressure and/or force exerted by the actuator, or to facilitate some other functionality. In another example, the controller module 672 may include instructions for operating the heater 610 to secure a body part relative to the biosensor 624 (e.g., by exerting a force or pressure via the flexible material of the actuator) and operating the biosensor 624 to detect one or more physiological parameters (e.g., an absorbance of blood in a portion of subsurface vasculature, a flow rate or velocity of blood in a portion of subsurface vasculature, an optical property of an implanted device that can be optically interrogated to detect an analyte or other physiological property) when the sensor 624 is secured relative to the body part. In yet another example, the controller module 672 may include instructions for operating the heater 610 to secure a body part relative to the injector 626 (e.g., by exerting a force or pressure via the flexible material of the actuator) and operating the injector 626 to penetrate skin of the body part (e.g., to deliver a device or substance, to access a blood sample) when the injector 626 is secured in contact with or otherwise secured relative to the body part.

Calculation and decision module 674 can include instructions for analyzing detected data (e.g., pressures detected using the pressure sensor 622) to determine a physiological property of a user and/or to determine if a medical condition or other specified condition is indicated, or other analytical processes relating to the environment proximate to the device 600 (e.g., based on information generated by additional sensors of the device 600). This could include determining a blood pressure based on detected pressures within the actuator (detected using the pressure sensor 622) as a pressure exerted on a body part, via the flexible material of the actuator, changes across a range of pressures.

The controller module 672 can also include instructions for operating a user interface 630. For example, controller module 672 may include instructions for displaying data collected by the pressure sensor 622 and/or biosensor 624 and analyzed by the calculation and decision module 674, or for displaying one or more alerts generated by the alert module 676. Controller module 672 may include instructions for displaying data related to a detected physiological parameter, a determined blood pressure, and/or a determined health state of a user. Further, controller module 672 may include instructions to execute certain functions based on inputs accepted by the user interface 630, such as inputs accepted by one or more buttons disposed on the user interface (e.g., to operate the heater 610 and pressure sensor 622 to detect a blood pressure, to operate the heater 610 and biosensor 624 to detect a physiological parameter, to operate the heater 610 and injector 626 to deliver a device or substance into a body and/or to access a blood sample from a body).

Communication platform 635 may also be operated by instructions within the controller module 672, such as instructions for sending and/or receiving information via a wireless antenna, which may be disposed on or in the device 600. The communication interface 635 can optionally include one or more oscillators, mixers, frequency injectors, etc. to modulate and/or demodulate information on a carrier frequency to be transmitted and/or received by the antenna. In some examples, the device 600 is configured to indicate an output from the processor by modulating an impedance of the antenna in a manner that is perceivable by a remote server or other remote computing device.

The computer readable medium 660 may further contain other data or information, such as medical and health history of a user of the device 600, a drug treatment regimen determined for a user of the device 600, that may be useful in operating the device 600 and/or determining whether a medical condition or some other specified condition is indicated. Further, the computer readable medium 660 may contain data corresponding to certain physiological parameter baselines, above or below which a medical condition is indicated. The baselines may be pre-stored on the computer readable medium 660, may be transmitted from a remote source, such as a remote server, or may be generated by the calculation and decision module 674 itself. The calculation and decision module 674 may include instructions for generating individual baselines for the user of the device 600 based on data collected by the device 600, e.g., based on a certain number blood pressure values determined from measurements of the pressure sensor 622. Baselines may also be generated by a remote server and transmitted to the device 600 via communication interface 630. The calculation and decision module 674 may also, upon determining that a medical or other emergency condition is indicated, generate one or more recommendations for the user of the device 600 based, at least in part, on consultation of a clinical protocol. Such recommendations may alternatively be generated by the remote server and transmitted to the device 600.

In some examples, the collected physiological property data, baseline profiles, health state information input by device users, and generated recommendations and clinical protocols may additionally be input to a cloud network and be made available for download by a user's physician. Trend and other analyses may also be performed on the collected data, such as blood pressure data and health state information, in the cloud computing network and be made available for download by physicians or clinicians.

Further, blood pressure and health state data from individuals or populations of device users may be used by physicians or clinicians in monitoring efficacy of a drug or other treatment. For example, high-density, real-time data may be collected from a population of device users who are participating in a clinical study to assess the safety and efficacy of a developmental drug or therapy. Such data may also be used on an individual level to assess a particular user's response to a drug or therapy. Based on this data, a physician or clinician may be able to tailor a drug treatment to suit an individual's needs.

In response to a determination by the calculation and decision module 674 that a medical or other specified condition is indicated (e.g., that a user is experiencing an acute hypertensive event, that a user is experiencing an acute hypotensive event), the alert module 676 may generate an alert via the user interface 630. The alert may include a visual component, such as textual or graphical information displayed on a display, an auditory component (e.g., an alarm sound), and/or tactile component (e.g., a vibration). The textual information may include one or more recommendations, such as a recommendation that the user of the device contact a medical professional, to seek immediate medical attention, or to administer a medication.

V. EXAMPLE METHODS

Figure 7:
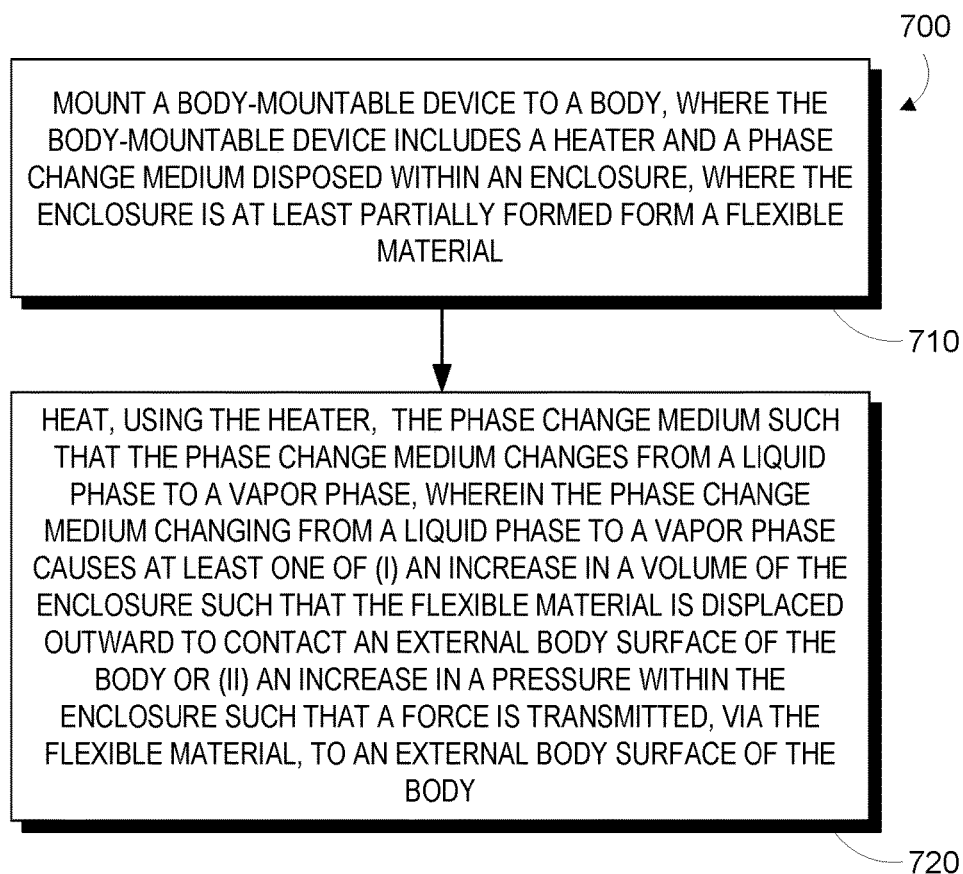
FIG. 7 is a flowchart of an example method.

FIG. 7 is a flowchart of a method 700 for operating a body-mountable device. The body-mountable device includes: (i) a mount for mounting the body-mountable device to an external body surface of a body (e.g., to skin of a wrist of a body), (ii) a heater, (iii) a phase change material that is in contact with the heater, and (iv) an enclosure that contains the heater and the phase change material and that is at least partially formed from a flexible material. The method 700 includes mounting the body-mountable device to an external body surface of a body (710). The body-mountable device could be a wearable device and mounting the device to a body (710) could include mounting the body-mountable device to and/or around a part of a body using a strap, adhesive, or some other means.

The method 700 also includes using the heater to heat the phase change material such that the phase change material changes from a liquid phase to a vapor phase, wherein the change of phase of the phase change material causes at least one of (i) an increase in a volume of the enclosure such that the flexible material is displaced outward to contact an external body surface of the body or (ii) an increase in a pressure within the enclosure such that a force is transmitted, via the flexible material, to an external body surface of the body (720). This could include applying the force to secure the location of the external body surface or the location of some other part of the body (e.g., portion of subsurface vasculature beneath the external skin surface) relative to element(s) of the body-mountable device, e.g., relative to a sensor or injector of the body-mountable device. The force could be exerted to control an amount of blood flow within a body part, e.g., to reduce blood loss from an injury, to control a blood flow rate in order to calibrate the determination of a blood pressure based on detected blood flow rates, or to facilitate some other application. The amount of force exerted could be controlled to change over time (e.g., by changing an amount of heat applied to phase change material using the heater over time) in order to, e.g., determine a blood pressure by detecting the pressure within the enclosure over time as the applied force changes.

The method 700 could include additional or alternative steps. The method 700 could include removing heat from the phase change material, e.g., using a heat pump. In some examples, the method 700 could include operating a sensor, an injector, or some other elements of the device when the force is being applied to the external body surface (e.g., when skin of the body is maintained in contact with a sensor or injector due to the applied force, when the location of a sensor relative to a portion of subsurface vasculature or other target within the body is secured due to the applied force). In some examples, the method 700 could include detecting a pressure within the enclosure (e.g., using a pressure sensor). Such a detected pressure could be used to control the amount of heat applied to the phase change material (720), e.g., to control an amount of force applied to a skin surface. Additionally or alternatively, the method 700 could include using the detected pressure to determine a blood pressure. In some examples, the method 700 could include determining a health state of a user based on such a determined blood pressure and/or based on some other physiological property detected by the device. In some examples, the method 700 could include indicating a determined blood pressure or other information about the operation of the system and/or about a detected or determined physiological property or health state to a user via a user interface of the device and/or indicating such information to a remote system (e.g., to a physician's computer, via a wireless or other communications link).

The example method 700 illustrated in FIG. 7 is meant as an illustrative, non-limiting example. Additional or alternative elements of the method and additional or alternative components of the system are anticipated, as will be obvious to one skilled in the art.

VI. CONCLUSION

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A body-mountable device comprising:
   a mount for mounting the body-mountable device to an external body surface;
   a heater;
   a phase change material, wherein the phase change material is in contact with the heater, and wherein the phase change material changes from a liquid phase to a vapor phase in response to being heated by the heater; and
   an enclosure, wherein the heater and the phase change material are disposed within the enclosure, wherein the enclosure is at least partially formed from a flexible material, wherein the phase change material changing from a liquid phase to a vapor phase in response to being heated by the heater causes at least one of (i) an increase in a volume of the enclosure such that the flexible material is displaced outward to contact the external body surface, or (ii) an increase in a pressure within the enclosure such that a force is transmitted, via the flexible material, to the external body surface.

2. The body-mountable device of claim 1, wherein the phase change material has a boiling point that is greater than approximately 37 degrees Celsius.

3. The body-mountable device of claim 1, wherein the heater comprises an electrically conductive mesh.

4. The body-mountable device of claim 1, wherein the flexible material of the enclosure comprises a lining comprising at least one of a metal or a metal oxide.

5. The body-mountable device of claim 1, further comprising a pressure sensor, wherein the pressure sensor is sensitive to a pressure within the enclosure.

6. The body-mountable device of claim 5, further comprising:
   a controller, wherein the controller is operably coupled to the heater and the pressure sensor, and wherein the controller is configured to perform controller operations comprising:
      operating the heater, during a first period of time, to provide heat at a first rate to the phase change material, wherein providing heat at the first rate causes the volume of the enclosure to increase such that the flexible material is in contact with the external body surface and such that a force is transmitted, via the flexible material, to the external body surface;
      operating the heater, during a second period of time, to provide heat at a second rate to the phase change material, wherein the second rate is less than the first rate, and wherein providing heat at the second rate causes a force transmitted, via the flexible material, to the external body surface to decrease over time during the second period of time;
      detecting, using the pressure sensor, the pressure within the enclosure multiple times during at least one of the first period of time or the second period of time; and
      determining a blood pressure based on the detected pressure within the enclosure.

7. The body-mountable device of claim 1, further comprising:
   a sensor; and
   a controller, wherein the controller is operably coupled to the heater and the sensor, and wherein the controller is configured to perform controller operations comprising:
      operating the heater to provide heat to the phase change material, wherein providing heat causes the volume of the enclosure to increase such that the flexible material is in contact with an external body surface and such that a force is transmitted, via the flexible material, to the external body surface, and wherein transmitting a force to the external body surface secures a location of the sensor relative to the body part;
      detecting, using the sensor, a property of a body to which the body-mountable device is mounted.

8. The body-mountable device of claim 1, further comprising:
   an injector; and
   a controller, wherein the controller is operably coupled to the heater and the injector, and wherein the controller is configured to perform controller operations comprising:
      operating the heater to provide heat to the phase change material, wherein providing heat causes the volume of the enclosure to increase such that the flexible material is in contact with the external body surface and such that a force is transmitted, via the flexible material, to the external body surface, and wherein transmitting a force to the external body surface secures a location of the injector relative to the body part;
      penetrating, using a needle of the injector, skin of the external body surface.

9. The body-mountable device of claim 1, further comprising thermal insulation, wherein the thermal insulation insulates the phase change material in the enclosure from an environment of the body-mountable device.

10. The body-mountable device of claim 1, further comprising a heat pump, wherein the heat pump is operable to remove heat from the phase change material in the enclosure.

11. The body-mountable device of claim 1, wherein a combined thickness of the heater and the flexible material of the enclosure is less than approximately 300 microns.

12. A system comprising:
    a heater;
    a phase change material, wherein the phase change material is in contact with the heater, and wherein the phase change material changes from a liquid phase to a vapor phase in response to being heated by the heater; and
    an enclosure, wherein the heater and the phase change material are disposed within the enclosure, wherein the enclosure is at least partially formed from a flexible material, wherein the phase change material changing from a liquid phase to a vapor phase in response to being heated by the heater causes at least one of (i) an increase in a volume of the enclosure such that the flexible material is displaced outward, or (ii) an increase in a pressure within the enclosure such that a force is transmitted via the flexible material.

13. The system of claim 12, wherein the heater comprises an electrically conductive mesh.

14. The system of claim 12, wherein the flexible material of the enclosure comprises a foil lining comprising at least one of a metal or a metal oxide.

15. The system of claim 12, further comprising thermal insulation, wherein the thermal insulation insulates the phase change material in the enclosure from an environment of the system.

16. The system of claim 12, wherein a combined thickness of the heater and the flexible material of the enclosure is less than approximately 300 microns.

17. A method comprising:
  mounting a body-mountable device to an external body surface of a body, wherein the body-mountable device comprises:
    a mount for mounting the body-mountable device to the external body surface;
    a heater;
    a phase change material, wherein the phase change material is in contact with the heater; and
    an enclosure, wherein the heater and the phase change material are disposed within the enclosure, wherein the enclosure is at least partially formed from a flexible material; and
  heating the phase change material using the heater such that the phase change material changes from a liquid phase to a vapor phase, wherein heating the phase change material such that the phase change material changes from a liquid phase to a vapor phase causes at least one of (i) an increase in a volume of the enclosure such that the flexible material is displaced outward to contact the external body surface, or (ii) an increase in a pressure within the enclosure such that a force is transmitted, via the flexible material, to the external body surface.

18. The method of claim 17, wherein heating the phase change material using the heater comprises: (i) providing heat, during a first period of time, at a first rate to the phase change material, wherein providing heat at the first rate causes the volume of the enclosure to increase such that the flexible material is in contact with the external body surface and such that a force is transmitted, via the flexible material, to the external body surface; and (ii) providing heat, during a second period of time, at a second rate to the phase change material, wherein the second rate is less than the first rate, and wherein providing heat at the second rate causes a force transmitted, via the flexible material, to the external body surface to decrease over time during the second period of time; and further comprising:
  detecting a pressure within the enclosure multiple times during at least one of the first period of time or the second period of time; and
  determining a blood pressure based on the detected pressure within the enclosure.

19. The method of claim 17, wherein the body-mountable device further comprises a sensor, wherein heating the phase change material using the heater comprises providing heat to the phase change material sufficient to cause the volume of the enclosure to increase such that the flexible material is in contact with the external body surface and such that a force is transmitted, via the flexible material, to the external body surface, and wherein transmitting a force to the external body surface secures a location of the sensor relative to the body part; and further comprising:
  detecting, using the sensor, a property of the body.

20. The method of claim 17, wherein the body-mountable device further comprises an injector, wherein heating the phase change material using the heater comprises providing heat to the phase change material sufficient to cause the volume of the enclosure to increase such that the flexible material is in contact with the external body surface and such that a force is transmitted, via the flexible material, to the external body surface, and wherein transmitting a force to the external body surface secures a location of the injector relative to the body part; and further comprising:
  penetrating, using a needle of the injector, skin of the external body surface.

* * * * *